United States Patent [19]

Sargent, III et al.

[11] Patent Number: 4,647,446

[45] Date of Patent: Mar. 3, 1987

[54] RAPID BRAIN SCANNING RADIOPHARMACEUTICAL

[75] Inventors: Thornton W. Sargent, III, Berkeley; Alexander T. Shulgin, Lafayette; Chester A. Mathis, Oakland, all of Calif.

[73] Assignee: The Regents of the University of California, Berkeley, Calif.

[21] Appl. No.: 732,517

[22] Filed: May 9, 1985

Related U.S. Application Data

[63] Continuation-in-part of Ser. No. 409,064, Aug. 18, 1982.

[51] Int. Cl.[4] .................. A61K 43/00; A61K 49/00; A61K 49/02
[52] U.S. Cl. .......................... 424/1.1; 424/9; 564/373; 564/374; 564/384; 568/308; 568/436
[58] Field of Search .................. 424/1.1, 9; 564/373, 564/374, 384; 568/436, 308

[56] References Cited

U.S. PATENT DOCUMENTS

| | | | |
|---|---|---|---|
| 3,344,023 | 9/1967 | Reinhold et al. | 568/308 |
| 4,113,850 | 9/1978 | Benes | 424/1 |
| 4,279,887 | 7/1981 | Baldwin et al. | 424/1.5 |
| 4,284,619 | 8/1981 | Lin | 424/1.5 |
| 4,287,368 | 9/1981 | Johnson et al. | 424/1.5 |
| 4,360,511 | 11/1982 | Baldwin et al. | 424/1.5 |
| 4,363,793 | 12/1982 | Blau et al. | 424/1 |

FOREIGN PATENT DOCUMENTS 1685  8/1980  World Int. Prop. O. .............. 424/1

OTHER PUBLICATIONS

Tramposch et al, J. Med. Chem., 26(2) 121-125 (1983).
Huang et al, J. Med. Chem., 22(4) 449-452 (1979).
Wang et al, Chem. Abstracts, 97 (1982) #211695w.
Sargent et al, Chem. Abstracts, 88 (1978) #101008f.
Carlson et al, Chem. Abstracts, 97 (1982) #98331j.
Holman, et al., Journal of Nuclear Medicine, vol. 24, 922 (1983).
Kuhl, et al., Journal of Nuclear Medicine, vol. 23, 196 (1982).
Sargent, et al. Comm. in Psychopharm., vol. 2, 1 (1978).
Braun, et al., Journal of Medicinal Chemistry, vol. 20, 1543 (1977).

List Continued on next page.

Primary Examiner—Christine M. Nucker
Attorney, Agent, or Firm—Flehr, Hohbach, Test, Albritton & Herbert

[57] ABSTRACT

A method for detecting the blood flow in animals, particularly in the brain, is provided wherein a detectable amount of a novel radioactive compound of the formula I is administered to one animal:

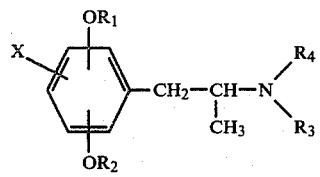

wherein $R_1$ and $R_2$ are independently alkyl of 1 to 6 carbon atoms or benzyl;
$R_3$ is alkyl of 1 to 6 carbon atoms, benzyl, cyclopropylalkyl of 4 to 6 carbon atoms, or cyanoalkyl of 2 to 6 carbon atoms;
$R_4$ is hydrogen, benzyl or alkyl of 1 to 6 carbon atoms;
with the provisos that $R_4$ is not isopropyl and when $R_4$ is methyl, $R_3$ is not benzyl;
and X is a radioactive halogen.

16 Claims, 2 Drawing Figures

OTHER PUBLICATIONS

Kalbhen, et al., *Int. Res. Com. System*, vol. 2, 1091 (1974).
Sargent, *Journal of Nuclear Medicine*, vol. 16, 243 (1975).
Sargent, et al. *Neuropharm.*, vol. 14, 165 (1975).
Richards, et al., *Int. Journal of Applied Radiation and Isotopes*, vol. 30, 250 (1979).
Winchell, et al., *Journal of Nuclear Medicine*, vol. 21, 940, 947 (1980).
Hill, et al., *Journal of Nuclear Medicine*, vol. 23, 191 (1982).
Sargent, et al., "Radiohalogen Labeled Imaging Agents. III: Compound for Measurement of Brain Blood Flow by Emission Tomography, to be published in J. of Med. Chem., Jun., 1984.
Braun, et al., *Journal of Labelled Compounds and Radiopharm.*, vol. XIV, No. 5, p. 767 (1978).
Sargent, et al., *J. of Nuclear Medicine*, vol. 19, No. 1, 71 (1978).
Baldwin, et al., *J. of Labelled Compounds and Radiopharm.*, vol. XIX, Nos. 11–12, 1305.
Sargent, et al., "A New Iodo-Amphetamine for Rapid Positron Tomographic Measurement of Brain Blood Flow with $^{122}$I, Oral Presentation, Third World Congress, Paris, France, 8/29–9/2/1982.

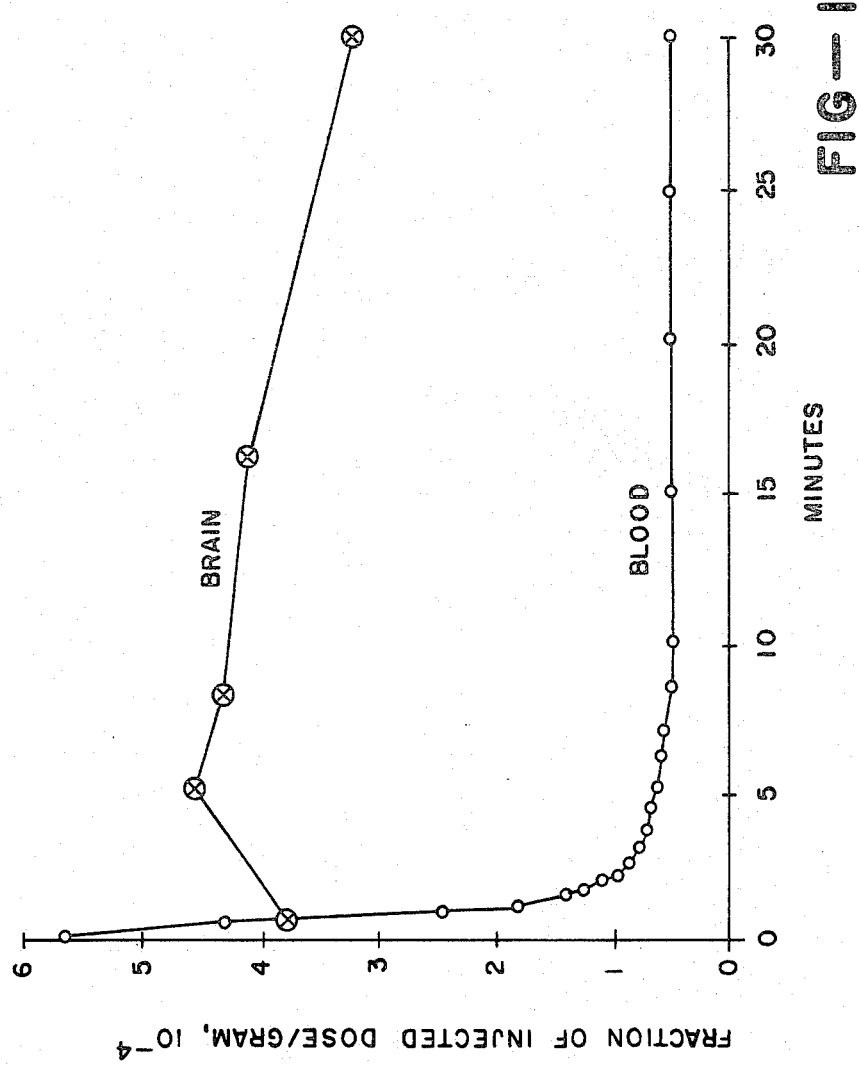

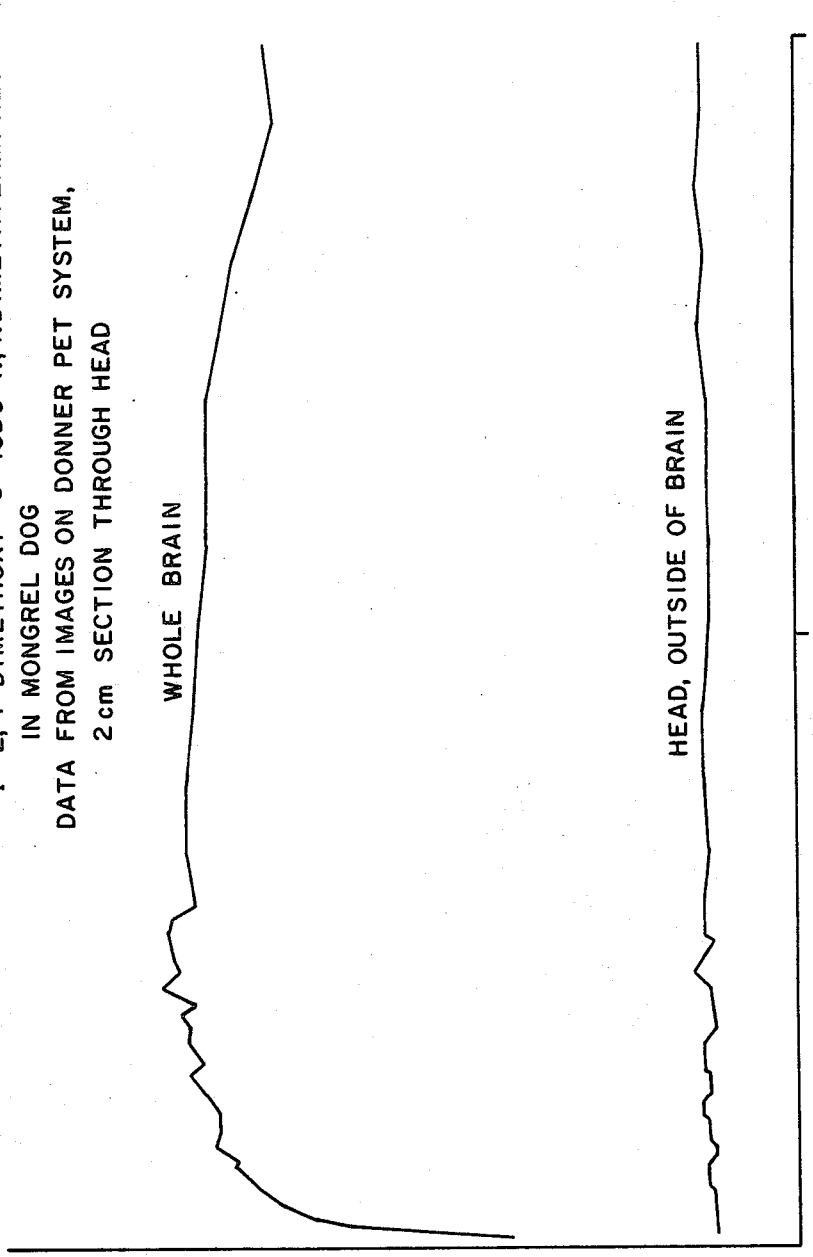

RAPID BRAIN SCANNING RADIOPHARMACEUTICAL

The government has rights in this invention pursuant to contract No. W-7405-ENG-48 awarded by the United States Department of Energy.

This is a continuation-in part of Ser. No. 409,064, filed Aug. 18, 1982.

The present invention is directed to radiopharmaceutical compounds and methods of use thereof in methods of measuring cerebral blood flow in mammals.

While gamma-emitting radiopharmaceutical compounds are known to be administered to a patient for purposes of therapy and/or diagnosis for determining their location and kinetics by means of external detection and imaging devices, such techniques have not been widely applied to studies on the mechanism of the action of drugs (pharmacodynamics), and particularly to pharmacodynamics in the brain. The use of gamma-emitting radiopharmaceuticals is important because such compounds yield continuous data on organ concentration of a suitably labelled material in an animal or human without disturbing normal body functions during the experiment. However, the time required to synthesize radiopharmaceuticals generally precludes the use of those with half-lives shorter than a few minutes, yet in some cases short-lived isotopes offer important advantages over those with longer half-lives. For example, a short-lived isotope exposes the patient to a lower radiation dose and allows the performance of repeat tests at a short interval of time or the following of one radiopharmaceutical investigation immediately by another one. Therefore, while conventional gamma-emitting radiopharmaceuticals may be useful for therapy or diagnosis, it is desirable in many cases to have short half-life radiopharmaceuticals. While Sargent et al., *Neuropharmacol* 14; 165–174 (1975), found that 4-bromo-2,5-dimethoxy-amphetamine, labelled with $^{77}Br$ or $^{82}Br$, concentrated in the brain, thereby having potential use as a brain scanning pharmaceutical, the high-energy gamma rays of the bromine isotope were found to limit resolution by gamma imaging devices. The use of iodine isotopes $^{131}I$ and $^{123}I$ emit lower energy gamma rays and are useful for imaging purposes, but it was found that when labeling the amphetamine derivative with iodine by dilution of non-radioactive iodide, the product had relatively low specific activity and also required a relatively long period of synthesis, i.e., at least 15 minutes. Furthermore, it was necessary to protect the amine function of the amphetamine derivatives in order to prevent oxidation by ICl, the labeling reagent. Therefore, the time required to remove the amine protection group precluded the use of short half-lived iodine isotopes.

It is therefore an object of the present invention to provide radiopharmaceutical compounds which are useful for pharmacodynamic investigations in mammals.

It is a further object of the present invention to provide novel pharmaceutical compounds which concentrate in the brain of mammals and are useful for the detecting of cerebral blood flow.

It is a further object of the present invention to provide a method of detecting cerebral blood flow in mammals utilizing radiopharmaceuticals which concentrate in the brain.

These and other objects will be apparent from the following description.

The present invention is directed to a method of measuring blood flow and a flow of other materials carried via blood, by administering to animals a radioactively labelled compound of the formula I:

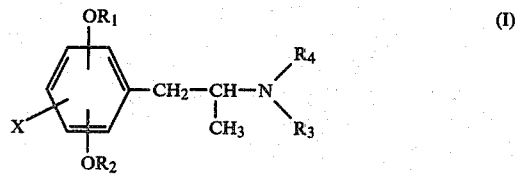

wherein
$R_1$ and $R_2$ are independently alkyl of 1 to 6 carbon atoms or benzyl;
$R_3$ is alkyl of 1 to 6 carbon atoms, benzyl, cyclopropylalkyl of 4 to 6 carbon atoms, or cyanoalkyl of 2 to 6 carbon atoms;
$R_4$ is hydrogen, benzyl or alkyl of 1 to 6 carbon atoms;
with the provisos that $R_4$ is not isopropyl and when $R_4$ is methyl, $R_3$ is not benzyl;
and X is a radioactive halogen.

The present invention further provides a method of preparing such compounds, particularly by utilization of novel intermediates which may be utilized to produce radioactive compounds of short half-lives.

In the accompanying FIGURES, FIG. 1 is a plot of the brain and blood radioactivity in a dog as a function of time after intravenous administration of $^{131}I$-2, 5-dimethoxy-4-iodo-N,N-dimethylamphetamine.

FIG. 2 is a plot of relative radioactivity detected in the brain and outside the brain in a cross-section through the head of a dog as a function of time after injection of $^{122}I$-2, 4-dimethoxy-5-iodo-N,N-dimethylamphetamine.

The compounds useful according to the present invention are radioactive compounds having the following formula (I)

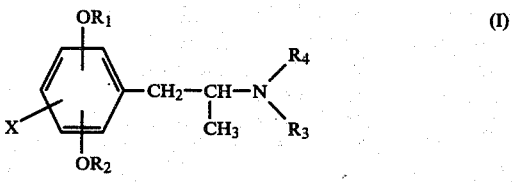

wherein
$R_1$ and $R_2$ are independently alkyl of 1 to 6 carbon atoms or benzyl;
$R_3$ is alkyl of 1 to 6 carbon atoms, benzyl, cyclopropylalkyl of 4 to 6 carbon atoms, or cyanoalkyl or 2 to 6 carbon atoms;
$R_4$ is hydrogen, benzyl of alkyl or 1 to 6 carbon atoms;
with the provisos that $R_4$ is not isopropyl and when $R_4$ is methyl, $R_3$ is not benzyl;
and X is a radioactive halogen. Both D and L stereoisomers are encompassed by the formulae herein.

Representative alkyl groups are methyl, ethyl, n-propyl, n-butyl, n-pentyl, isopentyl, neopentyl. Additionally, $R_1$, $R_2$ or $R_3$, but not $R_4$, may be isopropyl.

The group $R_3$ may also be cyclopropylalkyl, such as, cyclopropylmethyl, cyclopropylethyl or cyclopropylpropyl, or cyanoalkyl, such as, cyanomethyl, 1-cyanoethyl, 2-cyanoethyl, 3-cyanopropyl, 4-cyanobutyl or 5-cyanopentyl.

The radioactive isotope X may be a halogen atom. Particularly preferred are $^{122}I$, $^{123}I$, $^{124}I$, $^{125}I$, $^{131}I$, $^{74}Br$, $^{75}Br$, $^{76}Br$, $^{34m}Cl$, $^{18}F$. The iodine isotopes are most preferred, particularly $^{122}I$.

A preferred class of compounds according to the present invention comprises those in which $R_1$ and $R_2$ are methyl. The most preferred compound is the one in which $R_1$, $R_2$, $R_3$ and $R_4$ are all methyl.

Another preferred class of compounds according to the present invention is the class having the formula (II):

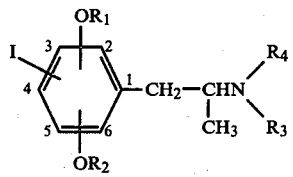

wherein $R_1$, $R_2$, $R_3$ and $R_4$ are as described above and I is a radioactive isotope, and the ring-subtituent positions are 2,4-dimethoxy-5-iodo, 3,5-dimethoxy-2-iodo, and 2,6-dimethoxy-3-iodo. A particularly preferred isotope is $^{122}I$.

The above compounds are useful for pharmacodynamic studies in mammals, particularly in the study of brain blood flow. The compounds according to the present invention may be useful as agents for positron or single photon imaging of the brain blood flow and for locating the sites of brain strokes. Once administered to an animal the radioactive compounds according to the present invention will concentrate in the brain and may be detectable by positron tomographic imaging or by other conventional devices capable of imaging gamma rays through animal tissue. The radioactive label used in the present compounds is preferably $^{122}I$ which has a half-life of 3.6 minutes and provides the subject with a low radiation dose. The short half-life of $^{122}I$ also permits flow measurements at intervals of 15–20 minutes and will allow repeat studies of the subject for measurement of changes in the regional cerebral blood flow after therapeutic intervention, or during controlled stimulation states. Other labels with longer half-lives may also be used, such as, $^{131}I$, $^{123}I$, and the like.

To produce compounds in accordance with the present invention, intermediates of the following formula III are prepared.

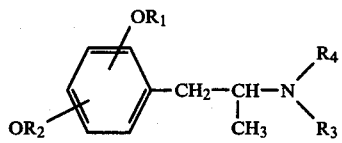

wherein $R_1$, $R_2$, $R_3$, $R_4$ are as defined hereinabove. To prepare compounds of formula III appropriate dialkoxyphenylisopropylamines are first prepared according to the method Braun et al., *Journal of Labeled Compounds and Radiopharmaceuticals*, 14; 767–773 (1978), the disclosure of which is incorporated herein by reference in its entirety. The dialkoxy-phenylisopropylamine may then be N-mono or di-alkylated according to known procedures. The intermediate of the formula III may then be radiolabelled to form compounds according to the present invention.

Alternatively, if a radioactive label is to be used having a relatively long half-life, such as $^{131}I$, the compounds according to the present invention may be made by reductive amination, using an appropriate amine, $NHR_3R_4$, of the intermediate IV having the following formula:

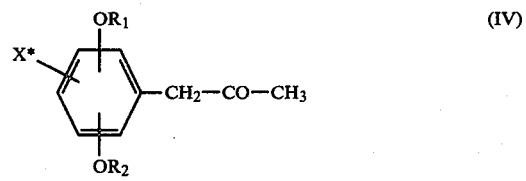

wherein $R_1$, $R_2$, $R_3$, and $R_4$ are as defined hereinabove and $X^*$ is a radioactive halide, such as $^{131}I$. The procedures for reductive amination are set forth by U. Braun, A. T. Shulgin and G. Braun, *J. Pharm. Sci.* 69: 192–195 (1980), the disclosure of which is incorporated herein by reference in its entirety. The intermediate III may be synthesized according to the procedures set forth in Examples 3–6 below.

The generator system for forming radioactive ICl is described by Richards et al., *Int. J. Appl. Radiat. Isotop.*, 30; 250 (1979), the disclosure of which is incorporated herein by reference in its entirety. The radioisotope $^{122}I$ is a positron-emitting radionuclide daughter of $^{122}Xe$. A chamber according to the method described by Richards et al. is provided with $Cl_2$ and $^{122}Xe$ and as the $^{122}Xe$ decays to form $^{122}I$, the following reaction takes place:

$$\tfrac{1}{2}Cl_2 + \tfrac{1}{2}I_2 = ICl$$

The ICl is reacted directly with the intermediate III to form the compounds according to the present invention. The reaction may be carried out in a suitable solvent, preferably glacial acetic acid and the reaction is complete in approximately one minute. The product is purified by conventional techniques, such as high pressure liquid chromatography or ion exchange chromatography.

An advantage of the present synthesis is that the precursor having the formula III is non-interfering because it is not labelled. Moreover, the iodine substitution appears to occur substantially at one position of the phenyl ring.

Yields of the iodination of III may be in the range of 80–90%.

Alternatively, a chamber according to the method described by Richards et al. may be evacuated and $^{122}Xe$ transferred to fill the vacuum. The $^{122}Xe$ decays to form $^{122}I-$ which attaches itself to the vessel wall, and the $^{122}Xe$ is removed. The $^{122}I-$ is put into aqueous solution and oxidized with an oxidant, such as Chloramine T, so that the $^{122}I$ reacts with III to form $^{122}I$-labelled products of the class II. Yields of up to 85% may be achieved by this method.

If a long lived radioactive label such as $^{131}I$ is desired, the radioactively-labelled intermediate III is formed within the reaction chamber, removed and purified by conventional procedures, and reductively aminated with an appropriate amine to produce compounds according to the present invention.

EXAMPLE 1

It has been found that when using an Anger Mark II whole-body Scanner, which is capable of imaging gamma rays with energies as high as 2.0 MeV over the entire body in a single scan, with a resolution of 20 mm., injections as low as 75 μCi of $^{131}$I labelled compounds of the present invention are detectable from regions of interest over the brain of a dog and a plurality of scans over 30 minutes may be taken. Referring to FIG. 1, there is shown data from a scan of a dog after injection of a compound of the present invention of 75 μCi (2,5-dimethoxy-4-($^{131}$I)-α,N,N-trimethylamphetamine). As it may be seen from FIG. 1, at the five-minute observed maximum in brain, 3.6% of the total body activity was located in the brain. The brain/blood ratio at five minutes was at 7.5 and reached a maximum of 8.7 after eight minutes.

EXAMPLE 2

The experiment set forth in Example 1 is repeated using the corresponding $^{122}$I-labelled compound. Labelling with $^{122}$I may be accomplished as described in Example 7.

EXAMPLE 3

To a solution of dimethoxybenzene (6.9 g) in 50 ml acetic acid was added over 3 minutes a solution of 20 g ICl in 20 ml acetic acid. The mixture was gradually heated on a steam bath for 2 hours. After 1 hour the formation of solids was evident. Heavy crystallization occurred after cooling with cold water. The crystalline solids were filtered washed with acetic acid to yield 16.7 g of a steel grey solid. The steel grey solids were suspended in about 200 ml water and solid $Na_2S_2O_4$ was added until the solids were white and flocculent. The white solids were filtered, washed with water and recrystallized from boiling acetonitrile (50 ml). A second recrystallization yielded white crystalline 2,5-diiodo-1,4-dimethoxybenzene, melting point 167°–168° C.

EXAMPLE 4

To a suspension of 19.2 g of the 2,5-diiodo-1,4-dimethoxybenzene prepared according to the procedure of Example 3 above, in 500 ml ether at 0° C. was added 33.6 ml of 1.6N butyl lithium in hexane. After stirring at 0° for 10 minutes, 8.0 ml N-methyl-formanilide was added. The mixture was stirred at 0° C. for 10 minutes then allowed to come to room temperature to a gentle reflux. The reaction mixture was then added to 800 ml water and 20 ml concentrated hydrochloric acid. After filtration and washing with ether, the filtrate was allowed to separate and the ether phase was collected and evaporated under vacuum to yield 22.0 g of a yellow solid. The solid was further dried under vacuum, collected, pressed onto a plate and washed with methanol. The solid was then ground to a powder with 20 ml methanol, filtered, washed with methanol and recrystallized from 60 ml boiling 95% ethanol and dried to yield 5.0 g yellow crystalline 2-formyl-5-iodo-1,4-dimethoxybenzene, melting point 134°–136° C.

EXAMPLE 5

To 4.8 g of the product made in accordance with the procedures of Example 4 above in 100 ml nitroethane was added 0.3 g ammonium acetate. The mixture was heated on a steam bath for 5½ hours, decanted from the solid residue and stripped. The resultant solid was collected in a beaker and crystallized from 20 ml boiling methanol. The crystals were collected and filtered to yield of 6.0 g crude solid. This crude solid was added to 0.6 g of crude product from a previous preparation and crystallized from 65 ml boiling methanol. The resultant crystals were filtered and air dried to yield 2.3 g gold crystalline 1-(4-iodo-2,5-dimethoxyphenyl)-2-nitro-prop-1-ene, melting point 117°–118° C.

EXAMPLE 6

To 2.1 g of the product made in accordance with the procedure of Example 5 above in 10 ml hot acetic acid was added 4 g electrolytic iron in 20 ml warm acetic acid. The mixture was heated on a steam bath to form a product comprising white solids and heavy black oil. The oil and solids were heated for one half hour with 500 ml water, filtered to remove iron and brown colored residues and washed with dichloromethane several times. The dichloromethane extracts were combined and washed with 5% sodium hydroxide. The dichloromethane was removed under vacuum to yield 3.9 g of a pale amber oil. This oil was distilled at 0.4 mm at 120°–130° C. to yield 1.1 g colorless oil which was collected in a flask. Scratching the flask produced crystalline 1-acetonyl-4-iodo-2,5-dimethoxybenzene. This may be converted to the $^{131}$I -labelled derivative by known iodine exchange methods, such as, by exchange with Na(+)$^{131}$I(−).

EXAMPLE 7

To generate $^{122}$Xe-$^{122}$I, a carrier-free xenon gas consisting of $^{122}$Xe is pumped into a liquid nitrogen cooled storage vessel, which is connected in a closed system to a storage vessel.

The reaction vessel is cooled with liquid nitrogen, and the storage vessel is then warmed to room temperature. The radioactive xenon is transferred by cryogenic pumping to the reaction vessel. In repeated tests, using a small geiger counter to monitor presence of radioactivity in each vessel, the xenon may be transferred from one vessel to the other in 10 seconds. After allowing 15 minutes for buildup of the $^{122}$I daughter in the reaction vessel, the xenon is transferred back to the storage vessel by cryopumping. Approximately 50 mCi of $^{122}$I has been measured remaining in the reaction vessel, identified by measuring the half-life at 3.5 minutes over two log cycles of decay.

The xenon gas consists of a carrier-free mixture of $^{127}$Xe, $^{125}$Xe, $^{123}$Xe and $^{122}$Xe as products of the bombardment of $^{127}$I with 68 MeV protons, from the reactions (p,n), (p,3n), (p,5n) and (p,6n) respectively. The proportion of each species of xenon at any time depends on the time after bombardment because of the different half-lives. To maximize the amount of $^{122}$I compared to the other xenon daughters $^{125}$I ($T_{\frac{1}{2}}$ 60 d) and $^{123}$I ($T_{\frac{1}{2}}$ 13 h), the holding time of the xenon in the reaction vessel is kept as short as possible, i.e. about 2 or 3 half-lives of $^{122}$I. For purposes of analysis of the chemical form of the radioactive iodine, a longer buildup time was allowed in order to accumulate the normally undesirable $^{125}$I, to utilize the more convenient 60 d half-life. A small quantity of precursor of the class II and Chloramine T are added in dilute phosphoric acid solution (0.2M). The $^{122}$I is oxidized by Chloramine T to form a reactive intermediate that reacts with II at 60° C. to form the desired product, an $^{122}$I-substituted-dialkoxy-N,N-dialkylamphetamine. The product is then purified by driving it through an anion exchange column by air pressure and collecting the correct fraction in the receiving vessel. An alternative reaction scheme instead of adding Chloramine T is to add $Cl_2$ to produce carrier-free $^{122}ICl$ which reacts with II at 140° C. in acetic acid.

Once transferred to the storage vessel, the radioxenon can be kept there for days at room temperature without release of radioactivity.

$Na^{125}I$ in dilute NaOH may be purchased from New England Nuclear Corporation. 2,4-Dimethoxybenzaldehyde and 3,5-dimethoxybenzaldehyde may be obtained commercially (Aldrich Chemical Co.).

2,4-Dimethoxy-$\beta$-methyl-$\beta$-nitrostyrene

A solution consisting of 25 g of 2,4-dimethoxybenzaldehyde (Aldrich) in 200 ml of nitroethane was treated with 0.5 g anhydrous ammonium acetate and held on a steam bath for 12 hours. The solvent was removed in vacuo from the mixture yielding 22.3 g of yellow crystals, m.p. 80°–81° C., upon cooling in 50 ml of methanol.

2,4-dimethoxybenzylmethyl ketone

A solution of 22 g of the above nitrostyrene in 200 ml warm glacial acetic acid was added to a suspension of 50 g of electrolytic iron dust in 200 ml glacial acetic acid. The mixture was heated on a steam bath until reaction commenced as evidenced by copious bubbling and frothing. The resulting paste was maintained on the steam bath for 2 hours after addition of an additional 100 ml of glacial acetic acid. The dark grey reaction mixture was quenched by the addition of 3 L water and the unreacted Fe removed by suction filtration. The filtered solids were washed with 100 ml $CH_2Cl_2$, the filtrate extracted with $3\times150$ ml $CH_2Cl_2$, the pooled organic extracts washed with 100 ml 5% NaOH and the solvent stripped in vacuo to yield 21.3 g of a pale straw-colored oil. The oil was distilled (125°–145° C./0.4 mm) yielding 12.7 g of the title ketone as a clear, colorless oil.

In the same manner, the 3,5-dimethoxybenzylmethyl ketone (colorless oil) may be prepared.

2,4-dimethoxy-$\alpha$-N,N-trimethylamphetamine

A solution of 12.4 g of the above ketone in 160 ml methanol was added to a warm solution of 35 g dimethylamine hydrochloride in 50 ml methanol. There was added 3.5 g sodium cyanoborohydride with vigorous stirring and a dropwise solution of conc. HCl-methanol (1:1) as needed to maintain the reaction at pH 6. Approximately 2 ml of the HCl/methanol solution was added over 3 days. The solvent was removed in vacuo and 2 L dilute sulfuric acid added to the residues and extracted with $2\times200$ ml $CH_2Cl_2$ (discarded), made basic with 200 ml 25% NaOH, and reextracted with $3\times150$ ml $CH_2Cl_2$.

The pooled extracts were stripped of solvent in vacuo yielding 16.1 g of a colorless oil which was distilled (105°–115° C., 0.4 mm) to yield 10.6 g of the title compound as a clear, colorless oil.

2,4-dimethoxy-5($^{122}I$)iodo-$\alpha$-N,N-trimethylamphetamine

Two ml of a 0.20M phosphoric acid solution containing 10 mg of 2,4-dimethoxy-$\alpha$-N,N-trimethylamphetamine (2,4-DNNA) and 100 micrograms of Chloramine T were added to a stainless steel loop on whose interior surface 30 mCi of $^{122}I$-iodide had been deposited by 40 mCi of $^{122}Xe$. The radiochemical yield of the title compound was 85% in this case (17 mCi). The characteristic retention times of the starting amine and product were 14 ml and 24 ml utilizing a 10 $\mu$m, 250$\times$4.6 mm Hamilton PRP-1 HPLC column eluted with methanol, 2M $NB_4OH$ and 1M $NH_4NO_3$ (650:50:25). The NMR of the product showed ortho/para splitting consistent with the 2,4-dimethoxy-5-I pattern (in $CDCl_3$; $\delta$(ppm) 0.91 (doublet 3H, $CH_3CH$), 2.34 (singlet, 6H, $(CH_3)_2N$); 2.76 (multiplet, 2H, $CH_2$), 2.85 (multiplet, 1H, $CHCH_3$), 3.83 (singlet, 3H, $CH_3O$), 3.88 (singlet, 3H, $CH_3O$), 6.40 (singlet, 1H, phenyl $C_3$-H), 7.43 (singlet, 1H, phenyl $C_6$-H).

The 5-$^{122}I$-2,4-dimethoxy-N,N-dimethylamphetamine prepared as above was injected into a dog that had been anesthetized and positioned in the Donner 280 crystal PET (position emission tomography) system, with the image plane as a coronal section through the head. The animal was first imaged after injection of $^{82}Rb$ from a $^{82}Sr$-$^{82}Rb$ generator, a diffusable tracer which concentrates in perfused tissues but does not cross the blood-brain barrier. FIG. 2 shows the number of counts in the brain region as a function of time after injection; the activity in brain reached a maximum at 2–3 minutes and remains constant until 8–10 minutes. The characteristics demonstrated in this example are those desired for a brain flow imaging radiopharmaceutical: rapid labeling chemistry, rapid incorporation into brain, maintenance of a constant level for sufficient time to obtain an image, rapid decay after the imagine time to reduce patient radiation dose and/or permit a second study within a short time and use of a positron-emitting isotope for utilization of PET imaging.

EXAMPLE 8

3-$^{122}I$-2,6-dimethoxy-N,N-dimethylamphetamine was prepared as follows:

2,6-Dimethoxy-$\beta$-methyl-$\beta$-nitrostyrene

A solution of 10.0 g of 2,6-dimethoxybenzaldehyde (prepared from resorcinol dimethyl ether, butyl lithium and N-methyl-formanilide) was dissolved in 50 ml nitroethane, treated with 0.5 g anh. ammonium acetate, and held on the steam bath for 2 h. Removal of the solvent in vacuo gave a heavy reddish oil which, upon dissolving in 25 ml methanol and cooling, yielded canary-yellow crystals, 12.0 g, m.p. 100°–102° C.

An analytical sample from methanol had m.p. 101.5°–102.5° C. Anal: C,H,N.

2,6-Dimethoxybenzylmethyl ketone

A solution of 11.5 g of the above nitrostyrene in 80 ml warm acetic acid was added to a suspension of 35 g electrolytic iron dust in 150 ml acetic acid. The mixture was heated on the steam bath until a vigorous reaction set in. The resulting paste was thinned with another 40 ml acetic acid, and heating was maintained for an hour. The reaction was quenched in 1.5 L water with stirring, decanted from unreacted Fe, and extracted with $3\times100$ ml $CH_2 Cl_2$. The pooled extracts were washed with 50 ml 5% NaOH, and the solvent was removed in vacuo to yield 10.5 g of a pale amber oil. This was distilled (95°–105° C./0.4 mm) yielding 8.7 g of the title ketone as a colorless oil. Anal: C,H.

2,6-Dimethoxy-$\alpha$-N,N-trimethylamphetamine

A solution of 7.6 g of the above ketone in 100 ml methanol was added to a (warmed) solution of 25 g dimethylamine hydrochloride in 60 ml methanol. With good stirring there was added 3.3 g NaCNBH$_3$, and conc. HCl dropwise as needed to maintain the reaction at about a pH of 6. When acid was no longer required (about 48 h) the methanol was removed in vacuo, and the residues poured into 2 L dilute sulfuric acid. The mixture was extracted with 2×100 ml CH$_2$Cl$_2$ (discarded), made basic with 25% NaOH, and reextracted (3×100 ml) with CH$_2$Cl$_2$. The pooled extracts were stripped of solvent yielding 2.38 g of a colorless oil which was distilled yielding 1.29 g of the title compound as a white oil. Anal: C,H,N.

2,6-Dimethoxy-3($^{122}$I)iodo-α-N,N-trimethylamphetamine

Two ml of an 0.20M phosphoric acid solution containing 10 mg of 2, 6-dimethoxy, N,N-trimethylamphetamine (2,6-DNNA) and 100 g of Chloramine T were added to a stainless steel loop on whose interior surface 30 mCi of $^{122}$I-iodide had been deposited by 40 mCi of $^{122}$Xe. The $^{122}$I had been allowed to accumulate for 15 min. and the $^{122}$Xe was removed by cryogenic pumping prior to the addition of the solution containing 2,6-DNNA. The stainless steel loop was heated to 60° C. within a few seconds by resistive heating and the reaction was allowed to proceed for 90 seconds at 60° C. The contents of the stainless steel loop were then pushed onto an 0.9 cm×4 cm anion exchange column (BioRad AG1-X8 acetate form) with 10 ml of an 0.10M pH 7.4 phosphate buffer solution. The 2, 6-dimethoxy-3-($^{122}$I)-α-N,N-trimethylamphetamine (30% radiochemical yield) was eluted in 10 ml of the neutral, buffered solution and unreacted $^{122}$-I-iodide (70%) remained on the anion exchange column. The entire radiochemical synthesis and product cleanup required approximately 2 min. and yielded 6 mCi of product. The assignment of the iodine substitution position, and the chromatographic characteristics of the title compound were established by a separate synthesis in the same manner but at millimolar scale. With HPLC, the starting amines and product had retention volumes of 9 ml and 20 ml on a Hamilton PRP-1 column eluted with methanol/2M NH$_3$/1 M NH$_4$NO$_3$ (650/50/25).

NMR of the product showed splitting consistent with a 2,6-dimethoxy-3-I pattern on the phenyl ring (in CDCl$_3$, δ(ppm) 6.46 (doublet, 1H, phenyl C$_5$-H, J$_{ORTHO}$=8.7 Hz) and 7.57 (doublet, 1H, phenyl C$_4$-H, J$_{ORTHO}$=8.7 Hz).

In the same manner, 3,5-dimethoxy-2-($^{122}$I)-iodo-α,N,N-trimethyl amphetamine may be prepared (68% incorporation of $^{122}$I removed from the loop). NMR (CDCl$_3$) δ0.99 (d, 3H, CH$_3$CH), 2.42 (6H, (CH$_3$)$_2$N), 2.66 (q, 2H, CH$_2$), 3.06 (m, 1H, CH$_3$CH), 3.80 (3H, CH$_3$O), 3.85 (3H, CH$_3$O), 6.30 (d, 1H, phenyl C$_6$-H, J$_m$=2.7 Hz), 6.43 (d, 1H, phenyl C$_4$-H, J$_m$=2.7 Hz).

In the same manner, 2,4-dimethoxy-5-($^{122}$I)-iodo-α,N,N-trimethyl amphetamine may be prepared (85% incorporation of $^{122}$I removed from the loop). NMR (CDCl$_3$) δ0.91 (d, 3H, CH$_3$CH), 2.34 (6H, (CH$_3$)$_2$N), 2.76 (m, 2H, CH$_2$), 2.85 (m, 1H, CHCH$_3$), 3.83 (3H, CH$_3$O), 3.88 (3H, CH$_3$O), 6.40 (1H, phenyl C$_3$-H), 7.43 (1H, phenyl C$_6$-H).

The compounds according to the present invention may be administered in any convenient method for introducing foreign substances into the blood stream of mammals. The weight dosage of the radioactive compounds does not appear to be critical and the lower weight dosage limit would be dependent only on the lower detection limits of the radioactive imaging device which is utilized. The radioactively-labelled compounds according to the present invention may be diluted by conventional pharmaceutical carriers for administration into the subject. Intravenous injection is the preferred method. The gamma ray imaging scanner may be a commercially available unit, such as, a Positron Emission Transaxial Tomograph, useful for scanning $^{122}$I, a Single Photon Emission Computerized Tomograph, useful for scanning $^{123}$I, or a conventional scintillation camera.

Having described the invention and particular specific embodiments thereof, we claim:

1. A radioactively labelled compound of the formula I:

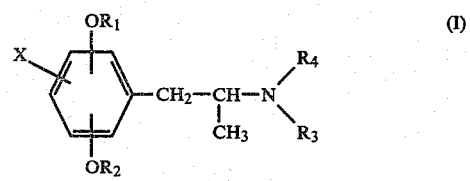

wherein

R$_1$ and R$_2$ are independently alkyl of 1 to 6 carbon atoms or benzyl;

R$_3$ is alkyl of 1 to 6 carbon atoms, benzyl, cyclopropylalkyl of 4 to 6 carbon atoms, or cyanoalkyl of 2 to 6 carbon atoms;

R$_4$ is hydrogen, benzyl or alkyl of 1 to 6 carbon atoms;

with the provisos R$_4$ is not isopropyl and when R$_4$ is methyl, R$_3$ is not benzyl;

and X is a radioactive halogen.

2. A compound according to claim 1 wherein X is $^{122}$I, $^{123}$I, $^{124}$I, $^{125}$I, $^{131}$I, $^{74}$Br, $^{75}$Br, $^{76}$Br, $^{34m}$Cl, or $^{18}$F.

3. A compound according to claim 2 wherein R$_3$ and R$_4$ are independently alkyl of 1 to 6 carbon atoms.

4. A compound according to claim 3 wherein X is $^{122}$I, $^{123}$I, $^{124}$I, $^{125}$I or $^{131}$I.

5. A compound according to claim 4 wherein R$_1$, R$_2$, R$_3$ and R$_4$ are methyl and X is $^{122}$I.

6. 2,4-Dimethoxy-5-iodo-N,N-dimethylamphetamine according to claim 5.

7. 2,6-Dimethoxy-3-iodo-N,N-dimethylamphetamine according to claim 5.

8. 3,5-Dimethoxy-4-iodo-N,N-dimethylamphetamine according to claim 5.

9. 2,4-Dialkoxy-5-halo-N,N-dialkylamphetamine according to claim 1.

10. 2,6-Dialkoxy-3-halo-N,N-dialkylamphetamine according to claim 1.

11. 3,5-Dialkoxy-2-halo-N,N-dialkylamphetamine according to claim 1.

12. A compound according to claim 9, 10 or 11 wherein R$_1$ and R$_2$ are methyl.

13. The compound according to claim 12 wherein R$_3$ and R$_4$ are methyl.

14. A compound according to claim 13 wherein R$_3$ and R$_4$ are alkyl of 1 to 6 carbon atoms.

15. A method of measuring cerebral blood flow in mammals comprising the step of administering to said animal a detectable amount of a radioactively labelled compound of the formula I:

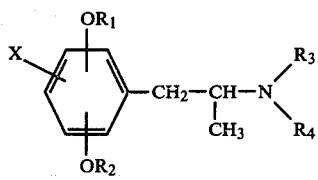

wherein

R₁ and R₂ are independently alkyl of 1 to 6 carbon atoms or benzyl;
R₃ is alkyl of 1 to 6 carbon atoms, benzyl, cyclopropylalkyl of 4 to 6 carbon atoms, or cyanoalkyl of 2 to 6 carbon atoms;
R₄ is hydrogen, benzyl or alkyl of 1 to 6 carbon atoms;
with the provisos that R₄ is not isopropyl and when R₄ is methyl, R₃ is not benzyl;
and X is a radioactive halogen.

16. A method according to claim 15 wherein said compound is administered intravenously.

* * * * *